United States Patent [19]

Hills et al.

[11] 4,443,375
[45] Apr. 17, 1984

[54] TETRAHYDROIMIDAZO(3,4-C)-1,3-DIAZO-CINE INTERMEDIATES FOR PRODUCTION OF GUANIDINES

[75] Inventors: Derek W. Hills, Welwyn Garden City; George R. White, Harpenden, both of England

[73] Assignee: Smith Kline & French Laboratories Limited, Welwyn Garden City, England

[21] Appl. No.: 436,894

[22] Filed: Oct. 26, 1982

Related U.S. Application Data

[62] Division of Ser. No. 270,072, Jun. 3, 1981, Pat. No. 4,375,435.

[51] Int. Cl.$^3$ ............................................. C07D 487/04
[52] U.S. Cl. ................................... 260/245.6; 544/281; 546/276; 548/198; 548/203; 548/205; 548/214; 548/324; 548/336
[58] Field of Search ....................... 548/324; 544/281; 260/246.6

[56] References Cited

U.S. PATENT DOCUMENTS 3,763,179  10/1973  Gall .................................. 260/245.6
4,013,659   3/1977  Durant et al. ....................... 424/263
4,233,302  11/1980  Martin-Smith et al. ............. 424/251

FOREIGN PATENT DOCUMENTS 1341375  4/1973  United Kingdom .

OTHER PUBLICATIONS

Derwent Abstract 33126C (EP 10418).
Derwent Abstract 53014B (EP 2930).
Chem. Abst. 61:5638(c) [Ackermann et al., Z. Physiol. Chem., 336(4–6), 283–284, (1964).]

Primary Examiner—Donald G. Daus
Assistant Examiner—G. Hendricks
Attorney, Agent, or Firm—Joan S. Keps; Richard D. Foggio; Alan D. Lourie

[57] ABSTRACT

This invention relates to a process for preparing imidazolylalkylguanidines, in particular N-[3-(4-imidazolyl)propyl]-N'-[2-(5-methyl-4-imidazolylmethylthio)ethyl]guanidine (impromidine) which has histamine $H_2$-agonist activity, to intermediates for use in this process and to processes for preparing these intermediates.

2 Claims, No Drawings

TETRAHYDROIMIDAZO(3,4-C)-1,3-DIAZOCINE INTERMEDIATES FOR PRODUCTION OF GUANIDINES

This is a division of application Ser. No. 270,072 filed June 3, 1981, now U.S. Pat. No. 4,375,435.

This invention relates to a process for preparing certain heterocyclyalkylguanidines, to intermediates for use in this process and to a process for preparing these intermediates.

In recent years it has been recognised that certain heterocyclylalkylguanidines possess useful biological activity. For example U.S. Pat. No. 4,013,659 discloses and claims compounds of formula (I):

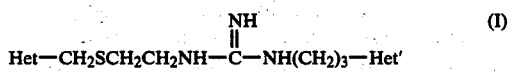

where Het is a 4-imidazolyl, 5-methyl-4-imidazolyl, 5-ethyl-4-imidazolyl, 5-halo-4-imidazolyl, 2-thiazolyl, 3-isothiazolyl, 4-halo-3-isothiazoyl, 2-pyridyl, 3-halo-2-pyridyl, 3-hydroxy-2-pyridyl, 3-methoxy-2-pyridyl or 3-ethoxy-2-pyridyl group and Het' is a 4-imidazolyl group; and hydrates, pharmaceutically acceptable salts and hydrated pharmaceutically acceptable salts thereof. The compounds of formula (I) have histamine $H_2$-receptor agonist activity.

Compounds of formula (I) have been prepared either by reacting a compound of formula (II) or (III):

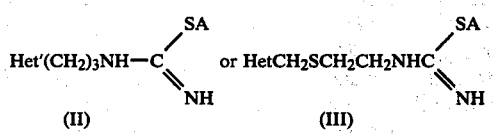

with a complementary amine of formula (IV) or (V):

Alternatively compounds of formula (I) were prepared by reacting a compound of formula (V) or (VII):

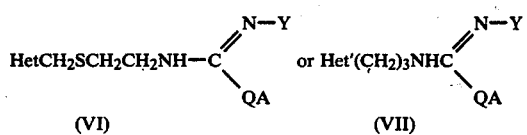

with a complementary amine of formula (IV) or (V) above to form a compound of formula (VIII):

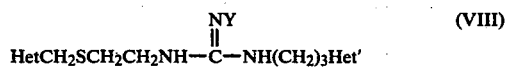

which is then converted into a compound of formula (I). In formulae (II) to (VIII) Het and Het' are as defined with reference to formula (I); A is alkyl, Q is oxygen or sulphur and Y is a group such that the compounds of formula (VIII) may be converted easily into the corresponding compound of formula (I), for example Y may be benzoyl or cyano.

We have now invented a process for preparing heterocyclylalkyl guanidines including those of formula (I) above with an improved degree of purity in particular the formation of bis compounds for example of formula (Ia):

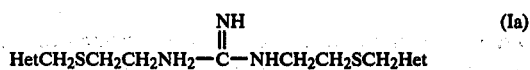

as biproducts is avoided.

Accordingly the present invention provides a process for preparing compounds of formula (IX):

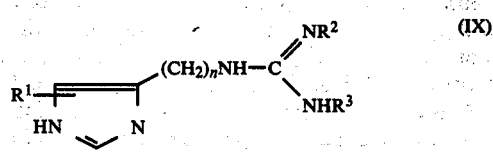

wherein $R^1$ is attached to a carbon atom in the imidazole moiety and is hydrogen, halogen or alkyl; $R^2$ is hydrogen, or a group convertible into hydrogen under acid conditions; $R^3$ is an optionally substituted alkyl group and n is 2, 3 or 4; which comprises reacting a compound of formula (X):

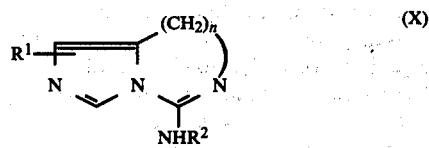

where n and $R^1$ are a defined with reference to formula (IX) and $R^2$ is a group convertible into hydrogen under acid conditions, with a compound of formula (XI):

where $R^3$ is as defined with reference to formula (IX) and thereafter optionally converting the group $R^2$ into hydrogen.

One particularly important compound which can be made by the process of this invention is N-[3-(4-imidazolyl)propyl]-N'-[2-(5-methyl-4-imidazolylmethylthio)ethyl]guanidine (impromidine) which is useful as a histamine $H_2$-agonist.

The nature and identity of $R^1$ are not critical to the success of the process, the group being selected having regard to the particular guanidine to be prepared.

Examples of halogens which $R^1$ represents are chlorine and bromine.

Examples of alkyl groups which $R^1$ represents are $C_{1-4}$ alkyl groups, particularly methyl.

Preferable $R^1$ occupies position 5 of the imidazolyl moiety.

In particular $R^1$ is hydrogen.

By way of example $R^2$ is benzoyl or cyano but preferably it is benzoyl.

Using the process of this invention, it is possible to introduce a wide variety of groups $R^3$. Thus the group $R^3$ may be selected on the basis of the properties whch it is desired that the product should possess.

$R^3$ may represent an alkyl group for example a $C_{1-4}$ alkyl group and particularly a methyl, ethyl or n-propyl group; or a phenyl substituted alkyl group, for example benzyl.

$R^3$ may also represent a substituted alkyl group of formula (XII):

$$Het^2(CH_2)_p Z(CH_2)_q-\qquad (XII)$$

where $Het^2$ is a 2-furanyl or 2-thienyl group optionally substituted in the 5-position with a group $R^5R^6N(CH_2)_r$- where $R^5$ and $R^6$ are $C_{1-4}$ alkyl or together with the nitrogen atom to which they are attached form a pyrrolidino, piperidino or morpholino group and r is 1 to 4; a 4-imidazolyl group optionally substituted in the 5-position with $C_{1-4}$ alkyl or halogen; a 2-pyridyl group optionally substituted in the 3-position with $C_{1-4}$ alkyl, $C_{1-4}$ alkoxy, halogen, amino or hydroxy; a 2-thiazolyl group or a 2-guanidino-4-thiazolyl group; Z is sulphur or methylene; when Z is sulphur p is 1 or 2 and q is 2 or 3 provided that p+q is 3 or 4 and when Z is methylene p is 0, 1 or 2 q is 2 or 3 and p+q is 2, 3 or 4.

With reference to formula (XII) examples of $C_{1-4}$ alkyl groups which $R^5$ and $R^6$ represent are methyl, ethyl, and n-propyl. Preferably $R^5$ and $R^6$ are methyl, particularly where r is 1.

When $Het^2$ is a 4-imidazolyl group substituted in the 5-position with $C_{1-4}$ alkyl or halogen preferably the substituents are methyl or bromine.

When $Het^2$ is a 2-pyridyl group substituted in the 3-position with $C_{1-4}$ alkyl, $C_{1-4}$ alkoxy, or halogen preferably the substituent is methyl, methoxy or bromine.

Preferably p is 1 and q is 2.
Preferably Z is sulphur.
Particular meanings of $R^3$ in formula (XII) are:
2-(2-guanidino-4-thiazolylmethylthio)ethyl-;
3-(4-imidazolyl)-propyl-4-(4-imidazolyl)butyl-;
4-(5-methyl-4-imidazolyl)butyl-;
2-(5-methyl-4-imidazolylmethylthio)ethyl;
2-(5-dimethylaminomethyl-2-furanylmethylthio)ethyl; and
2-(5-dimethylaminomethyl-2-thienylmethylthio)ethyl; of which 2-(5-methyl-4-imidazolylmethylthio)ethyl is important because it is present in the compound impromidine.

$R^3$ may also represent a substituted alkyl group of formula (XIII):-

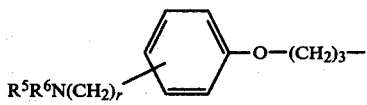

(XIII)

where the group $R^5R^6N(CH_2)_r$- is as defined with reference to formula (XII) and occupies the 3- or 4-position of the phenyl group.

Examples and preferred values of $R^5$, $R^6$ and r are as discussed above with reference to formula (XII).

A particular meaning of $R^3$ having formula (XIII) is:
3-(3-dimethylaminomethylphenoxy)propyl Generally the reaction can be carried out in a polar organic solvent, the choice of which is not critical to the success of the reaction provided that it is substantially inert to the reagents and product. Examples of suitable solvents are N,N-dimethylformamide and $C_{1-4}$ alkanols, particularly ethanol.

The reaction is generally carried out at moderate temperatures for example from room temperature to the reflux temperature of the solvent.

The period required for the reaction to proceed to completion depends upon the reaction condition. The reaction can be followed by standard techniques for example thin layer chromatography and is stopped when it is indicated that the reaction is substantially completed.

The product can then be isolated from the reaction mixture by conventional methods.

Compounds of formula (IX) where $R^2$ is a group convertible into hydrogen under acid condition, for example cyano or benzoyl, can be converted into the corresponding compounds of formula (IX) where $R^2$ is hydrogen by acid hydrolysis using for example a mineral acid in particular hydrochloric or sulphuric acid.

Compounds of formula (IX) above where n is 2 or 3 and $R^3$ is a group of formula (XII) or (XIII) are histamine $H_2$-agonists. Compounds of formula (IX) above where n is 4 and $R^3$ is a group formula (XII) or (XIII) are histamine $H_2$-antagonists.

Compounds of formula (IX) above where $R^3$ is a group of formula (XII) where Z, p and q are as previously defined; $Het^2$ is 2-guanidino-4-thiazolyl; n is 2,3 or 4, $R^2$ is hydrogen, cyano or benzoyl and $R^1$ is hydrogen, $C_{1-4}$ alkyl or halogen provided that n is 4 when $R^1$ and $R^2$ are hydrogen are described as histamine $H_2$-antagonists in European Patent Specification No. 0 010 418.

Compounds of formula (IX) above where $R^1$ is in position 5 and is hydrogen, $C_{1-4}$ alkyl or halogen $R^3$ is a group of formula (XII) where Z, p and q are as previously defined; $Het^2$ is 2-furanyl or 2-thienyl substituted with a group $R^5R^6N(CH_2)_r$ as previously defined; $R^2$ is hydrogen or cyano, n is 2, 3 or 4 and compounds of formula (IX) where $R^3$ is a group of formula (XIII) and n is 2, 3 or 4 are described as histamine $H_2$-antagonists in European Patent Specification No. 0 002 930.

The intermediates of formula (X) are novel and form a further aspect of the invention.

Specific intermediates of formula (X) are:
8-benzamido-4,5-dihydroimidazo(3,4-c)-1,3-diazepine and
9-benzamido-4,5,6,7-tetrahydroimidazo(3,4-c)-1,3-diazocine.

The intermediates (X) can be prepared by a process which comprises cyclising a compound of formula (XIV):

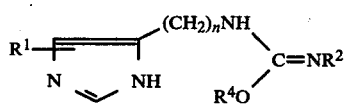

(XIV)

where $R^1$, $R^2$ and n are as defined with reference to formula (X) and $R^4$ is an optionally substituted aryl group where necessary in the presence of a non-nucleophilic base.

Preferably $R^2$ in the compound of formula (XIV) is benzoyl.

Examples of groups which $R^4$ represents are phenyl optionally substituted with one or more $C_{1-4}$ alkyl, $C_{1-4}$ alkoxy, halogen or nitro substituents.

Preferably $R^4$ is phenyl.

Examples of non-nucleophilic bases which can be used in this process are alkali metal and alkaline earth metal hydrides for example sodium and calcium hydride, alkali metal t-butoxides for example potassium t-butoxide and bicyclic diazalkenes for example 1,5-diazabicyclo(4.3.0)-non-5-ene and 1,5-diazabicyclo(5.4.0)undec-5-ene.

Preferably the base is sodium hydride.

When $R^2$ is cyano and n is 2 or 3 the base can be omitted. The reaction is generally carried out in a non-interfering polar organic liquid diluent or solvent choice of which is not critical to the success of the reaction provided that it is substantially inert to the reagents and product. Examples of such solvents include N,N-dimethylformamide and dimethylsulphoxide. When the base is a hydride the reaction medium must be dry.

The reaction is generally carried out at low temperatures for example 0° C. to room temperature, 5°–10° C. being preferred.

The time required for the reaction to go to completion depends upon the reagents employed and the precise reaction conditions. In any particular case the process can be monitored by a conventional technique for example thin layer chromatography and the reaction mixture worked up by conventional methods.

The intermediates of formula (XIV) can in turn be prepared by reacting an amine of formula (XV):

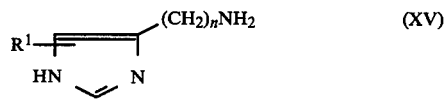

where $R^1$ and n are as defined with reference to formula (XIV); with a compound of formula (XVI):

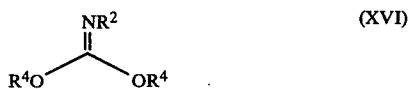

where $R^2$ and $R^4$ are as defined with reference to formula (XIV).

This reaction is generally carried out in a polar organic solvent, for example a halogenated hydro carbon, in particular methylene chloride and a $C_{1-4}$ alkanol, in particular ethanol at moderate to low temperature for example, less than 10° C. and preferably between 5° and 7° C.

The intermediates (XIV) particularly where $R^1$ and $R^4$ are as previously defined, $R^2$ is CN and n is 2 or 3 can cyclize in situ. Thus intermediates of formula (X) where $R^1$ is as previously defined, $R^2$ is CN and n is 2 to 3 can be prepared by reacting an amine of formula (XV) where $R^1$ as previously defined and n is 2 or 3 with a compound of formula (XVI) where $R^2$ is cyano and $R^4$ is as previously defined to form a compound of formula (XIV) where $R^1$ and $R^4$ are as previously defined, $R^2$ is CN, and n is 2 or 3 which is allowed to cyclise in situ.

The following Examples illustrate the invention.

EXAMPLES

EXAMPLE 1

(i) A solution of 4-methylhistamine was made in situ by adding the dihydrochloride (9.9 g) to a solution of sodium ethoxide in ethanol (from 2.3 g sodium and 50 ml ethanol) heating the mixture to reflux with stirring, cooling the mixture in ice and filtering the cooled solution to remove precipitated sodium chloride.

The 4-methylhistamine solution was added dropwise with stirring over 15 min to a cooled (5° C.) solution of diphenyl cyanoiminocarbonate (11.9 g) in methylene dichloride keeping the temperature between 5°–7° C. throughout the addition. When the addition was completed the reaction mixture was allowed to warm to room temperature with stirring over 30 min.

The mixture was extracted with sodium bicarbonate solution (5% w/v), the organic phase was dried over magnesium sulphate and the solvent evaporated yielding an oil which solidified on trituration with diethyl ether. The solid was dissolved in boiling ethanol and precipitated with n-hexane yielding 7-cyano-3,4-dihydroimidazo(3,4-c)-1,3-pyrimidine (4.0 g) m.p. 249°–250° C.

(ii) A mixture of 2-(5-methyl-4-imidazolylmethylthio)-ethylamine (2.5 g) and 7-cyano-3,4-dihydroimidazo(3,4-c)-1,3-pyrimidine (2.23 g) in ethanol (50 ml) where heated under reflux for 20 hr. The ethanol was evaporated leaving a oily residue which on addition of water formed a white crystalline solid which was recrystallised from water yielding N-cyano-N'-[2-(5-methyl-4-imidazolyl)ethyl]-N''-[2-(5-methyl-4-imidazolylmethylthio)ethyl]guanidine (2.10 g) m.p. 190°–191° C.

EXAMPLE 2

(i) A solution of 3-(4-imidazolyl)propylamine in ethanol was prepared in situ from the dihydrochloride (4.95 g) by the method of Example 1 (i) with a solution of sodium ethoxide (from 1.15 g sodium and 50 ml ethanol) in ethanol.

The 3-(4-imidazolyl)propylamine solution was added dropwise with stirring over 15 min to a cooled (5° C.) solution of diphenyl benzoyliminocarbonate (7.93 g) in dichloromethane (75 ml), keeping the reaction temperature between 5°–7° C. throughout the addition. When the addition was complete the mixture was allowed to warm to room temperature over 30 min with stirring. The volume of the mixture was evaporated to 25 ml poured into water (250 ml) and chilled for ca 16 hr. The white solid which deposited was recrystallised from aqueous ethanol yielding N-benzoyl-N-[3-(4-imidazolyl)propyl]-O-phenyl isourea (6.06 g) as a white crystalline solid.

(ii) N-benzoyl-N-(3-(4-imidazolyl)propyl)-O-phenyl isourea (5.0 g) was added to a stirred suspension of sodium hydride (0.5 g NaH, weighed as a 50% dispersion in oil and washed before use with b.p. 40°–60° petroleum ether) in dry dimethylformamide (50 ml). The addition was carried out over 10 min with cooling, keeping the temperature between 5° and 10° C. The reaction mixture was stirred for a further 10 minutes and then allowed to warm to room temperature. Stirring was continued until T.L.C. (SiO$_2$ plate F$_{254}$; eluted with EtOAc: MeOH: NH$_4$OH s.g. 0880 (5:1:1) indicated that the reaction was complete. The reaction mixture was poured into water, and allowed to stand over-night. The precipitated product was filtered, washed and recrystallised by dissolving in ethanol (30 ml) filtering through diatomaceous earth diluting the filtrate with an equal volue of water, and allowing the diluted filtrate to stand overnight at 10° C. The product was isolated by filtration and dried yielding 8-benzamido-4,5-dihydroimidazo(3,4-c)-1,3-diazepine (2.31 g) m.p. 158°–160° C.

EXAMPLE 3

(i) A solution of 4-(4-imidazolyl)butylamine (1.39 g) in ethanol (25 ml) was added dropwise with stirring over 10 min to a solution of diphenyl benzoylimino carbonate (3.17 g) in dichloromethane (25 ml) with cooling to maintain the temperature at between 5°–6° C. When the addition was completed the reaction mixture was stirred for a further 30 min without cooling. The volume of the reaction mixture was reduced to 10 ml by evaporation and the residue was washed with water by decantation yielding N-benzoyl-N-[4-(4-imidazolyl)-butyl]-O-phenyl isourea which was used without purification in the next stage.

(ii) A solution of N-benzoyl-N-[4-(4-imidazolyl)-butyl]-O-phenyl isourea (2.51 g) in dimethylformamide (15 ml) was added dropwise with stirring over 10 min to a suspension of sodium hydride (0.5 g; weighed as a 50% dispersion in oil) in dimethylformamide (10 ml), keeping the temperature at between 5°–7° C. throughout the addition. The mixture was then stirred for 30 min at room temperature and poured into water (200 ml). An oil deposited which solidified. The solid was filtered and recrystallised from ethanol/diethyl ether giving 9-benzamido-4,5,6,7-tetrahydroimidazo(3,4-c)diazocine (1.05 g) m.p. 102°–103° C.

EXAMPLE 4

A solution of 3-(4-imidazolyl)propylamine in ethanol (400 ml) was made in situ from the dihydrochloride (4.0 g) and sodium ethoxide (from 0.92 g sodium and 400 ml ethanol) by the method of Example 1 (i). This solution was added dropwise with stirring over 15 min to a solution of diphenyl cyanoiminocarbonate (4.76 g) in dichloromethane (40 ml) keeping the temperature between 5°–7° C. throughout the addition.

When the addition was complete the reaction mixture was allowed to warm to room temperature and to stir for a further hour. Dichloromethane was evaporated leaving an ethanolic residue to which water was added causing an oil to deposit. The oil was washed with water by decantation and chilled. The oil solidified giving 8-cyanoamino-4,5-dihydroimidazo(3,4-c)diazepine m.p. 210°–215° C.

EXAMPLE 5

A solution of 2-(5-methyl-4-imidazolylmethylthio)ethylamine in ethanol (50 ml) was prepared from the dihydrochloride (2.53 g) and sodium ethoxide in ethanol (from sodium 0.51 g and ethanol 50 ml) as described in Example 1(i). To this was added 8-benzamido-4,5-dihydroimidazo(3,4-c)diazepine (2.54 g). The mixture so obtained was refluxed for 20 hr cooled, filtered and the solution evaporated leaving a residue which was triturated with water yielding N-benzoyl-N'-[3-(4-imidazolyl)propyl]-N''-[2-(5-methyl-4-imidazolylmethylthio)ethyl] guanidine as a white solid m.p. 98.5°–100° C.

EXAMPLE 6

(i) A mixture of 8-benzamido-4,5-dihydroimidazo(3,4-c)diazepine (2.54 g) and 4-(4-imidazolyl)butylamine in ethanol (25 ml) were refluxed for 5 hr. The ethanol was evaporated and the residue was triturated with water, dried and triturated with diethyl ether. The residue solidified yielding crude N-benzoyl-N'-[3-(4-imidazolyl)propyl]-N''-[4-(4-imidazolyl)butyl]guanidine which was used in the next step without purification.

(ii) N-Benzoyl-N'-[3-(4-imidazolyl)propyl]-N''-[4-(4-imidazolyl)butyl]guanidine (3.9 g) was refluxed overnight with conc. hydrochloric acid (50 ml). The excess of hydrochloric acid was evaporated yielding a residue containing crude N-[3-(4-imidazolyl)propyl]-N'-[4-(4-imidazolyl)butyl]guanidine trihydrochloride which was characterised as the tripicrate as follows. The residue was diluted with water and extracted with diethylether to remove benzoic acid. The aqueous phase was separated and an excess of aqueous sodium picrate solution was added to it. This deposited a yellow solid which was recrystallised from aqueous acetone yielding N-[3-(4-imidazolyl)propyl]-N'-[4-(4-imidazolyl)butyl]guanidine tripicrate m.p. 206°–208° C.

EXAMPLE 7

Reaction of 2-(5-dimethylaminomethyl-2-furanylmethylthio)ethyl amine with 8-cyanoamino-4,5-dihydroimidazo-(3,4-c)diazepine prepared as described in Example 4 yields N-cyano-N'[3-(4-imidazolyl)propyl]-N''-[2-(5-dimethylaminoethyl-2-furanylmethylthio)ethyl guanidine. This can be hydrolysed with dilute hydrochloric acid to yield N-[3-(4-imidazolyl)propyl]-N'-[2-(5-dimethylaminomethyl-2-furanylmethylthio)ethyl]guanidine trihydrochloride which is characterised by conversion into the picrate. m.p. 144°–146° C.

EXAMPLE 8

Reaction of 2-(5-dimethylaminomethyl-2-thienylmethylthio)ethyl amine with 8-cyano-4,5-dihydroimidazo(3,4-c)diazepine prepared as described in Example 4 yields N-cyano-N'-[3-(4-imidazolyl)propyl]-N''-[2-(5-dimethylaminomethyl-2-thienylmethylthio)ethyl]guanidine. This can be hydrolysed with dilute hydrochloric acid to yield N-[3-(4-imidazolyl)propyl]-N'-[2-(5-dimethylaminomethyl-2-thienylmethylthio)ethyl]guanidine trihydrochloride which is characterised by conversion to the picrate.

EXAMPLE 9

N-Benzoyl-N'-[3-(4-imidazolyl)propyl]-N''-[2-(5-methyl-4-imidazolylmethylthio)ethyl]guanidine (2.37 g) was heated overnight on a steam bath with conc. hydrochloric acid (135 ml). The aqueous reaction mixture was evaporated to ca 75% of its original volume to remove the excess of hydrogen chloride. The aqueous residue obtained was extracted with diethyl ether to remove benzoic acid. The aqueous phase was evaporated at reduced pressure and azeotroped with ethanol (100 ml). The oily residue was recrystallised from ethanol to yield N-[3-(4-imidazolyl)propyl]-N'-[2-(5-methyl-4-imidazolyl methylthio)ethyl]guanidine trihydrochloride (1.93 g) m.p. 200°–201° C.

We claim:

1. A compound of formula (X)

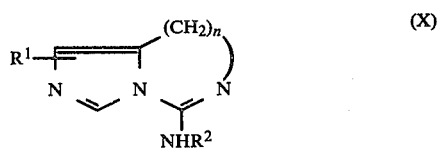

where n is 4;

R$^1$ is attached to a carbon atom in the imidazole moiety and is hydrogen, halogen or alkyl; and R$^2$ is cyano or benzoyl.

2. A compound according to claim 1 which is 9-benzamido-4,5,6,7-tetrahydroimidazo (3,4-c)-1,3-diazocine.

* * * * *